(12) United States Patent
Kim et al.

(10) Patent No.: US 11,046,970 B2
(45) Date of Patent: Jun. 29, 2021

(54) **DIAT GENE DERIVED FROM *ORYZA SATIVA* CONTROLLING DROUGHT STRESS TOLERANCE OF A PLANT AND USES THEREOF**

(71) Applicant: SEOUL NATIONAL UNIVERSITY R&DB FOUNDATION, Seoul (KR)

(72) Inventors: Ju-Kon Kim, Gangwon-do (KR); Youn Shic Kim, Gyeonggi-do (KR); Jae Sung Shim, Gangwon-do (KR); Hyein Jeong, Incheon (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/516,541

(22) Filed: Jul. 19, 2019

(65) Prior Publication Data

US 2021/0017533 A1 Jan. 21, 2021

(51) Int. Cl.
*C12N 15/82* (2006.01)
*C12N 15/52* (2006.01)

(52) U.S. Cl.
CPC ......... *C12N 15/8273* (2013.01); *C12N 15/52* (2013.01)

(58) Field of Classification Search
None
See application file for complete search history.

(56) References Cited

U.S. PATENT DOCUMENTS

| 4,940,838 A | 7/1990 | Schilperoort et al. |
| 2015/0150158 A1* | 5/2015 | Reuzeau ............ C12N 15/8261 800/287 |

FOREIGN PATENT DOCUMENTS

| EP | 0 116 718 B1 | 5/1990 |
| EP | 0 120 516 B1 | 10/1991 |
| KR | 10-1427180 B1 | 8/2014 |
| KR | 10-1915296 B1 | 11/2018 |

OTHER PUBLICATIONS

Roosens et al, Molecular Breeding 9:73-80, 2002 (Year: 2002).*
B. Sylvia de Pater et al., "The promoter of the rice gene GOS2 is active in various different monocot tissues and binds ice nuclear factor ASF-1", The Plant Journal, vol. 2 (6), pp. 837-844, 1992.
In-Cheol Jang et al., "Subcellular targeting of green fluorescent protein to plastids in transgenic rice plants provides a high-level expression system", Molecular Breeding, vol. 5, pp. 453-461, 1999.
Shouichi Yoshida et al,. "Laboratory Manual for Physiological Studies of Rice", The International Rice Research Institute, 1976.

* cited by examiner

*Primary Examiner* — Elizabeth F McElwain
(74) *Attorney, Agent, or Firm* — The PL Law Group, PLLC

(57) ABSTRACT

A method for controlling drought stress tolerance of a plant includes transforming a cell of the plant with a recombinant vector which includes a gene encoding *Oryza sativa*-derived DIAT (Drought-Induced AminoTransferase) protein to control expression of the gene encoding the DIAT protein. As the drought stress tolerance of a plant can be enhanced by the DIAT gene of the present invention, it is expected that a plant having drought stress tolerance is developed and used for enhancement of the productivity of crops.

4 Claims, 5 Drawing Sheets

Specification includes a Sequence Listing.

DIAT GENE DERIVED FROM ORYZA SATIVA CONTROLLING DROUGHT STRESS TOLERANCE OF A PLANT AND USES THEREOF

GOVERNMENT LICENSE RIGHTS

This invention was made with government support under Next-Generation BioGreen 21 (R&D) Program (Project NO. PJ013662012019) awarded by the Rural Development Administration, Republic of Korea. The government has certain rights in the invention.

TECHNICAL FIELD

The present invention relates to *Oryza sativa*-derived DIAT gene controlling the drought stress tolerance of a plant, and uses thereof.

BACKGROUND ART

Drought stress is a major destructive form of environmental stress adversely affecting crop productivity worldwide. Recent global climate change increases chance of occurrence and degree of severity of drought in agriculturally important area. This has motivated efforts to improve crop productivity by manipulating drought tolerance mechanisms.

To cope with drought stress, plants have evolved protective mechanisms that allow them to acclimate to drought stress. Metabolic acclimation via the accumulation of compatible osmolyte has long been thought as one of general protective strategies under drought conditions in plants. Compatible osmolytes are known to induce tolerance under drought conditions by adjusting osmotic balance, protecting structure of proteins and maintaining membrane integrity. For these reasons, molecular characterization and engineering of biosynthesis mechanisms of compatible osmolyte have been in the spotlight for improving drought tolerance in plants.

Amino acid and its metabolism provide stress tolerance in plants through accumulation of compatible osmolyte. The three essential amino acids isoleucine, leucine and valine, collectively called as branched-chain amino acids (BCAA) due to the short branched carbohydrate residues, have also been found to be highly accumulated in response to drought stress in plants. It has been proposed that BCAAs contribute to induce tolerance of plants by acting as a compatible osmolyte or an alternative energy source.

BCAA biosynthesis has a unique feature because a set of four identical enzymes catalyzes the reaction with different substrates to synthesize corresponding BCAAs. Acetohydroxyacid synthase (AHAS, EC 4.1.3.18) is responsible for the first step of BCAA synthesis and catalyzes condensation of two pyruvates, as well as pyruvate and 2-ketobutyrate. Ketol-acid reductoisomerase (KARI, EC 1.1.1.86) and dihydroxyacid dehydratase (DHAD, EC 4.2.1.9) sequentially catalyze the next two steps to produce branched-chain 2-oxo acids. The final transamination step in BCAA biosynthesis is catalyzed by the branched-chain amino acid aminotransferase (BCAT, EC 2.6.1.42). BCATs have been thought a key regulator of BCAA accumulation under stress conditions due to their stress-inducible expression patterns and correlation with BCAA levels. The inventors of present invention isolated the DIAT (Drought-Induced AminoTransferase) from rice (Oryza sativa), and analyzed the function of the gene regarding drought tolerance.

Meanwhile, in Korean Patent Registration No. 1427180, '*Oryza sativa*-derived OsCTR1 gene for enhancing drought stress tolerance of a plant and uses thereof' is disclosed, and, in Korean Patent Registration No. 1915296, '*Oryza sativa*-derived OsPHYB gene for controlling salt stress tolerance of a plant and uses thereof' is disclosed. However, *Oryza sativa*-derived DIAT gene for controlling drought stress tolerance of a plant and uses thereof of the present invention have not been described before.

SUMMARY

The present invention is devised in view of the above-described needs. The inventors of the present invention found that the expression of DIAT (Drought-Induced AminoTransferase) gene of *Oryza sativa* plant is induced under drought conditions. The inventors produced a transgenic rice plant which overexpresses DIAT gene by transformation of rice plants with a recombinant vector comprising a gene encoding DIAT protein derived from rice, and found that the transgenic plant which overexpresses DIAT gene has enhanced tolerance to drought stress compared to a non-transgenic plant. It was also found that, compared to a non-transgenic plant, content of branched chain amino acids, which function as compatible osmolytes has significantly increased in a transgenic plant. The present invention is completed by confirming enhancement of drought tolerance and BCAA contents by overexpression of DIAT in transgenic rice plants.

To solve the problems that are described above, the present invention provides a method for controlling drought stress tolerance of a plant including transforming a plant cell with a recombinant vector which contains a gene encoding the *Oryza sativa*-derived DIAT (Drought-Induced AminoTransferase) protein.

The present invention further provides a method for producing a transformed plant with controlled drought stress tolerance including transforming a plant cell with a recombinant vector which includes a gene encoding the *Oryza sativa*-derived DIAT protein; and regenerating a plant from the transformed plant cell.

The present invention further provides a transformed plant with controlled drought stress tolerance which is produced by the aforementioned method, and a transformed seed thereof.

The present invention further provides a composition for controlling drought stress tolerance of a plant which contains, as an effective component, a gene encoding the *Oryza sativa*-derived DIAT protein consisting of the amino acid sequence of SEQ ID NO: 2.

As the drought stress tolerance of a plant can be enhanced by the DIAT gene of the present invention, it is expected that a plant having drought stress tolerance is developed and used for enhancement of the productivity of crops.

BRIEF DESCRIPTION OF THE DRAWINGS

FIG. 2a to FIG. 2g show the result of analyzing the drought stress tolerance of a transgenic plant which overexpresses DIAT gene, in which FIG. 2a shows the result showing the relative expression levels of DIAT gene in a non-transgenic *Oryza sativa* plant (NT, Dongjin variety) or four independent lines (#1, #5, #48, and #61) of DIAT-overexpressing transgenic rice plants (GOS2::DIAT), FIG. 2b shows the result of measuring moisture levels in soils planted with NT or DIAT-overexpressing transgenic rice plants, FIG. 2c shows a photographic image showing the appearance of plants after drought stress treatments followed by re-watering, FIG. 2d shows the result of determining the survival rate of NT and DIAT-overexpressing transgenic rice plants after re-watering, FIG. 2e shows the result of analyzing Fv/Fm value in accordance with the drought stress treatments, and FIG. 2f and FIG. 2g show the results of analyzing the agricultural traits of DIAT-overexpressing transgenic rice plants to determine the drought tolerance of the DIAT-overexpressing transgenic rice plants in field conditions are shown. In the figures, PH represents plant height; CL represents culm length; PL represents panicle length; NP represents number of filled grains; FR represents filling rate; and TGW represents total grain weight.

In FIG. 4, (a) shows the treatment with leucine only, (b) shows the treatment with isoleucine only, (c) shows the treatment with valine only, (d) shows the simultaneous treatment with leucine, isoleucine, and valine, in which (e) BCAAs indicates simultaneous treatment of leucine, isoleucine, and valine, while Mock represents distilled water treatment without any branched chain amino acids.

DETAILED DESCRIPTION

Figure 1:
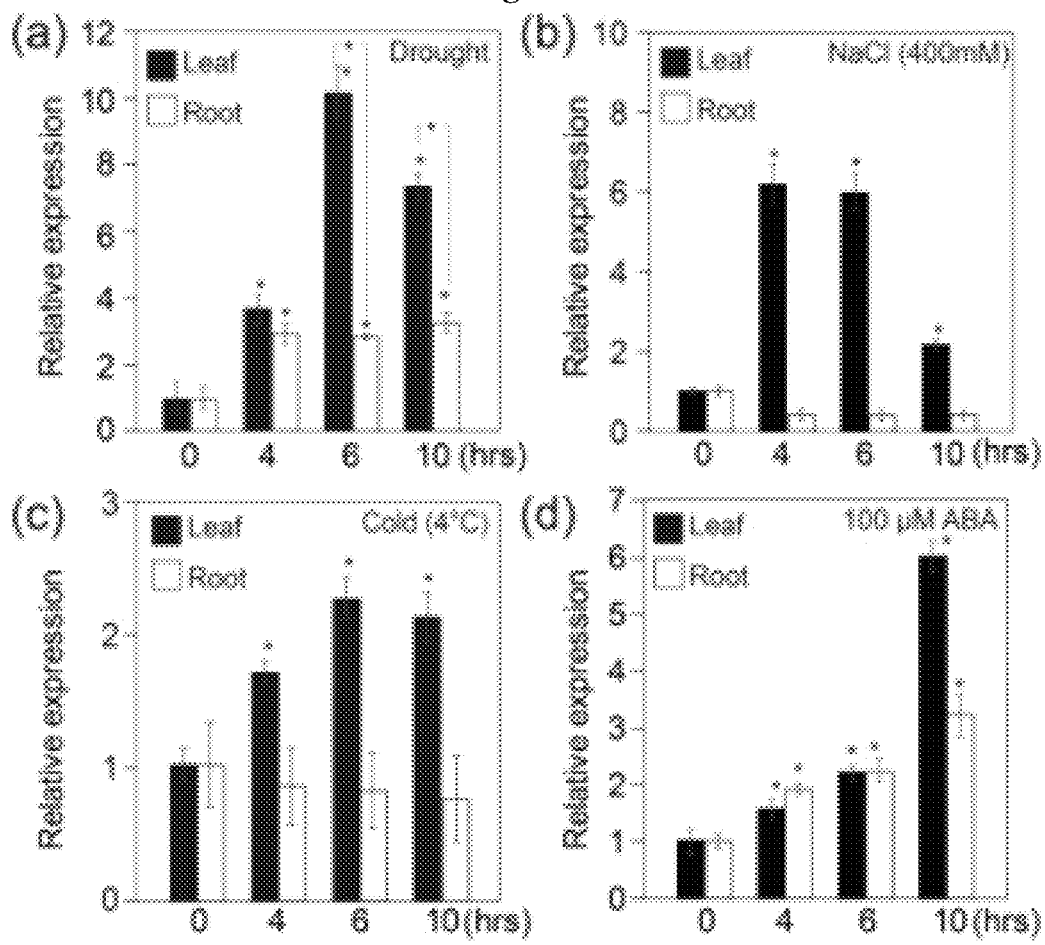
FIG. 1 shows the results of determining the expression level of the DIAT gene in leaf and root tissues of *Oryza sativa* after treatment of a plant with (a) drought stress, (b) salt stress, (c) low temperature stress, or (d) abscisic acid (ABA) as a stress hormone.

To achieve the object of the present invention, the present invention provides a method for controlling drought stress tolerance of a plant including transforming a plant cell with a recombinant vector which includes a gene encoding the *Oryza sativa*-derived DIAT (Drought-Induced AminoTransferase) protein to control the expression of the gene encoding the DIAT protein.

Included in the scope of the DIAT protein of the present invention are a protein having the amino acid sequence represented by SEQ ID NO: 2, which is isolated from rice (*Oryza sativa*), and functional equivalents of the protein. The term "functional equivalents" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it indicates a protein exhibiting substantially the same activity as the protein represented by SEQ ID NO: 2. The expression "substantially the same activity" means the activity of a plant for controlling drought stress tolerance. Also included in the present invention are fragments, derivatives, and analogues of the DIAT protein.

The terms "fragments", "derivatives", and "analogues" that are described in the present specification indicate a polypeptide with the substantially same biological function or activity as the DIAT protein of the present invention.

This gene encoding the DIAT protein of the present invention has a characteristic of controlling the drought stress tolerance of a plant, and genomic DNA, cDNA, and synthetic DNA encoding the DIAT protein are all within the scope of the gene. Preferably, the gene encoding the DIAT protein of the present invention may include the nucleotide sequence of SEQ ID NO: 1. Furthermore, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

The method according to one embodiment of the present invention is to enhance the drought stress tolerance of a plant by transforming a plant cell with a recombinant vector containing the gene of SEQ ID NO:1 to overexpress *Oryza sativa*-derived DIAT gene, but it is not limited thereto.

The expression "overexpress a gene" means that the gene is overexpressed to the level that is higher than the expression level in a wild type plant. As a method for introducing the gene into a genome, there is a method for transforming a plant by using an expression vector, in which the gene under regulation of a promoter is included.

In the present specification, the term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

The term "vector" is used herein to refer DNA fragment (s) and nucleotide molecules that are delivered to a cell. Vector can replicate DNA and be independently reproduced in a host cell. The terms "delivery system" and "vector" are often interchangeably used.

The vector of the present invention can be constructed as a vector which is typically used for cloning or expression. In addition, the vector of the present invention can be constructed by having a prokaryotic cell or an eukaryotic cell as a host. For example, when the vector of the present invention is an expression vector and a prokaryotic cell is employed as a host, a strong promoter for the initiation of transcription (e.g., pLλ promoter, trp promoter, lac promoter, T7 promoter, tac promoter and the like), and a ribosome binding site for the initiation of translation and a termination sequence for transcription/translation are generally comprised. When *E. coli* is employed as a host cell, a promoter and an operator region relating to the biosynthetic pathway of tryptophan in *E. coli,* and left-side promoter of phage λ (i.e., pLλ promoter) can be used as a regulation site.

For the recombinant vector according to the present invention, the promoter may be any of CaMV 35S promoter, actin promoter, ubiquitin promoter, pEMU promoter, MAS promoter, and histone promoter, but not limited thereto.

In the present specification, the term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, the constitutive promoter can be preferable for the present invention. Therefore, a possibility for choosing the constitutive promoter is not limited herein.

The recombinant vector of the present invention can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

Preferred example of the recombinant vector of the present invention is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid DNA sequence to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded virus, and a viral vector which can be originated from Gemini virus, etc., for example a non-complete plant viral vector. Use of said vector can be advantageous especially when a host plant cannot be easily transformed.

The recombinant vector may comprise at least one selective marker. Said selective marker is a nucleotide sequence having a property of being selected by a common chemical method. Examples include all genes that are useful for distinguishing transformed cells from non-transgenic cells. Specific examples thereof include a gene resistant to herbicide such as glyphosate and phosphinothricin, and a gene resistant to antibiotics such as kanamycin, G418, bleomycin, hygromycin, and chloramphenicol, and aadA gene, but not limited thereto.

For the recombinant vector of the present invention, any conventional terminator can be used. Examples include nopaline synthase (NOS), rice α-amylase RAmyl A terminator, a phaseolin terminator, a terminator for optopine gene of *Agrobacterium tumefaciens*, rrnB1/B2 of *Escherichia coli* or the like, but are not limited thereto.

Any plant cell can be employed as the "plant cell" that is used for transformation of a plant. The plant cell may be cultured cells, cultured tissues, cultured organs, or whole plant, preferably cultured cells, cultured tissues, or cultured organs, and more preferably cultured cells in any form. The "plant tissue" may be either differentiated or undifferentiated tissues of a plant, and examples thereof include, although not limited thereto, root, stem, leaf, pollen, seed, tumor tissue, and cells in various forms that are used for culture like single cell, protoplast, shoot, and callus tissue. The plant tissue can be either in planta, or in a state of organ culture, tissue culture, or cell culture.

Also provided by the present invention is a method for producing a transformed plant with controlled drought stress tolerance including:

transforming a plant cell with a recombinant vector including a gene encoding the *Oryza sativa*-derived DIAT protein; and regenerating a plant from the transformed plant cell.

The *Oryza sativa*-derived DIAT protein according to the present invention may consist of the amino acid sequence of SEQ ID NO: 2, and the gene encoding the *Oryza sativa*-derived DIAT protein may consist of the nucleotide sequence of SEQ ID NO: 1, but it is not limited thereto.

With regard to the method for producing a transformed plant with controlled drought stress tolerance, scope of the DIAT protein and DIAT gene is as described in the above.

According to the method for producing a transformed plant of one embodiment of the present invention, by increasing the expression of the gene encoding *Oryza sativa*-derived DIAT protein in a transformed plant, a transformed plant having enhanced drought stress tolerance compared to a non-transgenic plant can be produced.

Furthermore, the method for the present invention also includes regenerating a transformed plant from the transformed plant cells. Any method well known in the pertinent art may be used as a method for regenerating a transformed plant from the transformed plant cells. The transformed plant should be re-differentiated to a whole plant. For many various species, techniques for re-differentiation of a mature plant from culture of callus or protoplast are well known in the pertinent art.

Also provided by the present invention is a transformed plant produced by the above production method which has controlled drought stress tolerance stress, and a transformed seed thereof.

As described in the above, for a case in which the expression of a gene encoding the DIAT protein consisting of the amino acid sequence of SEQ ID NO: 2 is enhanced, the transformed plant of the present invention is characterized to have enhanced drought stress tolerance.

In one embodiment of the present invention, the plant can be preferably a monocot plant such as rice, barley, wheat, rye, corn, sugar cane, oat, or onion, or a dicot plant such as Arabidopsis thaliana, potato, eggplant, tobacco, pepper, tomato, burdock, crown daisy, lettuce, balloon flower, spinach, chard, yam, carrot, water parsley, Chinese cabbage, cabbage, Raphanus sativus for. raphnistroides MAK, watermelon, oriental melon, cucumber, zucchini, gourd, strawberry, soybean, mung bean, kidney bean, or sweet pea. However, it is not limited thereto.

Also provided by the present invention is a composition for controlling drought stress tolerance of a plant which contains, as an effective component, a gene for encoding the *Oryza sativa*-derived DIAT protein consisting of the amino acid sequence of SEQ ID NO: 2. The composition contains, as an effective component, a gene for encoding the *Oryza sativa*-derived protein consisting of the amino acid sequence of SEQ ID NO: 2, and by transforming a plant cell with a recombinant vector including this gene, the drought stress tolerance of a plant can be controlled.

Hereinbelow, the present invention is explained in greater detail in view of the Examples. However, it is evident that the following Examples are given only for exemplification of the present invention and by no means the present invention is limited to the following Examples.

Materials and Methods

1. Plasmid Construction and Transformation of *Oryza sativa*

CDS (coding sequence) of DIAT (Os05g0244700) was amplified by using total RNA extracted from rice (variety: Nipponbare) as a template and also DIAT forward primer (5'-CACCATGCAAGGGGAACACCATGACCA-3'; SEQ ID NO: 3) and DIAT reverse primer (5'-CTAGCTCGCTTGATCATAAGGA-3'; SEQ ID NO: 4). The amplified DIAT CDS and GOS2 promoter (Pater et al., The Plant Journal, 1992, 2(6), 837-844) were used for producing GOS2:: DIAT vector for rice transformation by using Gateway System (Invitrogen, USA). GOS2::DIAT vector was transformed into rice plants by Agrobacterium (LBA4404) mediated co-cultivation method (Jang et al., Mol. Breeding, 1999, 5, 453-461).

2. Treatment with Stress and Abscisic Acid

In order to analyze the expression pattern of DIAT gene in response to abiotic stresses, non-transgenic (NT, 'Dongjin' variety) rice plant was sown on a MS (Murashige-Skoog) medium and cultured for 4 days at 28° C. dark conditions. Seedlings were transferred to a plant growth chamber [light cycle: 16/8h (light/dark), luminosity: 200 µmol m$^{-2}$ s$^{-1}$, humidity: 70%] and then further incubated for 3 days. One-week-old seedlings were transferred to a liquid medium (Yoshida et al., Laboratory manual for physiological studies of rice, 1976, pp. 61) and further grown for 2 weeks. In order to induce drought stress in 3-week-old non-transgenic plant, the entire plant was air-dried for 10 hours. For salt and cold stress treatments, whole plants were transferred to a 400 mM sodium chloride solution, or exposed to 4° C. temperature for 10 hours. For the analysis of the DIAT expression patterns in response to ABA, the entire 3-week old plant was transferred to a solution containing 100 µM abscisic acid for 10 hours.

3. Real-Time Quantitative RT-PCR

Leaf and root tissues were collected from a plant which has been applied with abiotic stress and abscisic acid, and then frozen with liquid nitrogen. Total RNA was extracted using Hybrid-R RNA purification kit (GeneAll, Korea). Total RNA (2 µg) was used to synthesize first strand cDNA using RevertAid M-MuLV Reverse Transcriptase (Thermo Scientific, USA). To analyze the gene expression levels, quantitative RT-PCR (qRT-PCR) was carried out by using Mx3000p Real-time PCR device and 2× Real-Time PCR smart mix (SolGent, Korea). Rice Ubiquitin1 transcript was used as an internal control for normalization, and each of the information of the primers used for carrying out the quantitative qRT-PCR and conditions for qRT-PCR is shown in the following Table 1 and Table 2.

TABLE 1

Primer Sequence Information

| Gene Name | Nucleotide sequence (5'→3') (SEQ ID NO:) |
|---|---|
| DIAT (sOs05g0244700) | F: TCGAGCCATTCCTGCACTTG (SEQ ID NO: 5)<br>R: TCGAGCCATTCCTGCACTTG (SEQ ID NO: 6) |
| Ubi1 (Os06g06814010) | F: ATGGAGCTGCTGCTGTTCTA (SEQ ID NO: 7)<br>R: TTCTTCCATGCTGCTCTACC (SEQ ID NO: 8) |

TABLE 2

| PCR Condition | | |
|---|---|---|
| Step | Temperature (° C.) | Time (seconds) |
| Pre-denaturation | 95 | 600 |
| Denaturation | 95 | 30 |
| Annealing | 60 | 30 |
| Extension | 72 | 30 |

Repeat additional 40 times after returning to the denaturation step

4. Drought Stress Treatments and Tolerance Evaluation

DIAT overexpressing transgenic and non-transgenic (NT) control plants (*O. Sativa* cv. Dongjin) were sown on MS solid medium and incubated in a dark growth chamber for 4 days at 28° C. Seedlings were then transferred to growth chamber with light and dark cycle of 16 h light/8 h dark and grown for 1 additional day before transplanting to soil. Thirty plants from each line were transplanted into ten soil pots (4×4×6 cm: three plants per pot) within a container (59×38.5×15 cm) and grown for additional 4 weeks in a greenhouse (16 h light/8 h dark cycle) at 30° C. Drought stress was imposed by sequentially withholding water for 3 days and re-watering for 7 days. Drought-induced symptoms were monitored by imaging transgenic and NT plants at the indicated time points. The soil moisture contents were measured at indicated time points using the SM150 Soil Moisture Sensor (Delta-T Devices).

Transient chlorophyll a fluorescence and performance index were measured using the Handy-PEA fluorimeter (Hansatech Instruments). Two-week-old plants were transplanted in soil pot (15×15×14 cm) and grown for 5 weeks. Chlorophyll A fluorescence were measured from longest leaves of each plant after 1 hour of dark adaptation to ensure sufficient opening of the reaction center. Measurement was performed at apex, middle, and base regions of leaves using the Handy-PEA fluorimeter. Thirty measurements per line were averaged using the HANDY-PEA software (version 1.31).

To evaluate yield components of the DIAT-overexpressing transgenic and NT plants under field growth conditions, three independent lines of the GOS2::OsAT-IV plants and NT plants were planted in the rice paddy field at Kyungpook National University, Gunwi (36°06'48.0"N,128°38038.0"E), Korea. Yield parameters were scored from 20 plants collected from three different plots for normal field conditions. To evaluate yield components of the plants under field drought conditions, plants were grown in semi-field conditions under rain-off shelters. Plants were exposed to intermittent drought twice by withholding water during panicle development stage. Drought treatment was monitored by measuring soil water content using Soil Moisture Sensor. After two rounds of drought treatment at the reproductive stage, the plants were re-irrigated until harvesting stage. Yield components were scored from 18 plants for each line for drought field conditions.

5. Quantification of Branched Chain Amino Acids

To measure the amino acid contents, non-transgenic (*O. Sativa* cv. Dongjin) and DIAT-overexpressing transgenic plants {GOS2::OsAT-IV (#5)} were sown on MS solid medium and incubated in a dark growth chamber for 4 days at 28 ° C. Seedlings were then transferred to growth chamber with light and dark cycle of 16 h light/8 h dark for 2 weeks. 2-week-old rice seedlings were transferred to Yoshida solution and incubated for additional 1 week. 3-week-old rice plants were then air-dried to simulate dehydration stress and sampled at indicated time points after stress treatment.

Plants not exposed to stress were used as control. Amino acid contents were measured using HPLC Ultimate 3000 equipped with column VD Spher 100 C18—E (4.6 mm×150 mm, 3.5 um/VDS, Optilab) and FL detector 1260 FLD (Agilent) in the National Instrumentation Center for Environmental Management, College of Agriculture and Life Science, Seoul National University.in Seoul National University. Data represented mean±SD of two biological replicates.

6. Branched Chain Amino Acids and PEG Treatment

Three-week-old non-transgenic rice plants grown in liquid media (Yoshida et al., Laboratory manual for physiological studies of rice, 1976, pp. 61) were fed with 10 mM L-valine, leucine or isoleucine (Sigma) by dipping its roots in a solution containing BCAAs for 24 hrs. Plants were then transferred to a 50 ml tube containing 25 mL of 25% PEG 8000 (Sigma) solution. Plants pre-treated with BCAAs were harvested for amino acid analysis. PEG-induced visual symptoms such as leaf rolling and wilting were monitored by imaging NT and transgenic plants at the indicated time points.

EXAMPLE 1

Analysis of Expression Pattern of DIAT Gene Under Abiotic Stress Conditions

As a result of analyzing the expression level of DIAT gene in wild type Oryza sativa, it was found that, compared to the control group without stress treatment, expression level of DIAT gene has increased in accordance with an increase in the time of treatment with drought stress ((a) of FIG. 1), high salt stress ((b) of FIG. 1), low temperature stress ((c) of FIG. 1), and abscisic acid stress ((d) of FIG. 1), and, in most cases, the expression amount of DIAT gene has more significantly increased in leaves compared to roots.

EXAMPLE 2

Determination of Drought Tolerance Caused by Overexpression of DIAT Gene

Figure 2A:
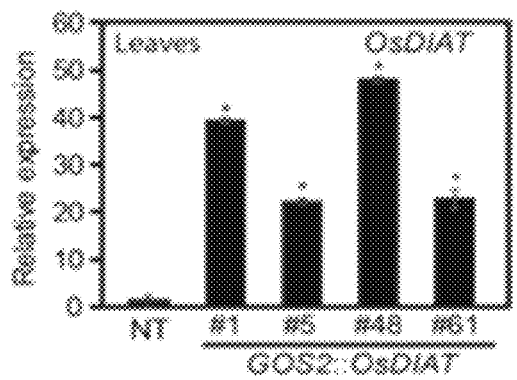
Figure 2B:
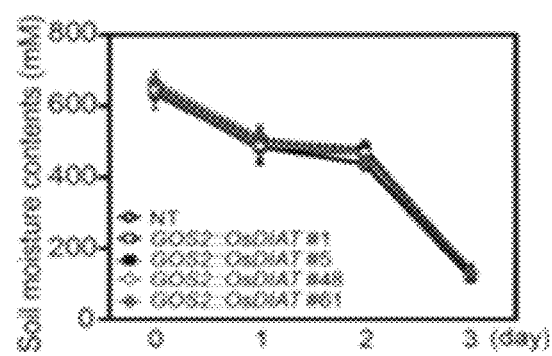
Figure 2C:
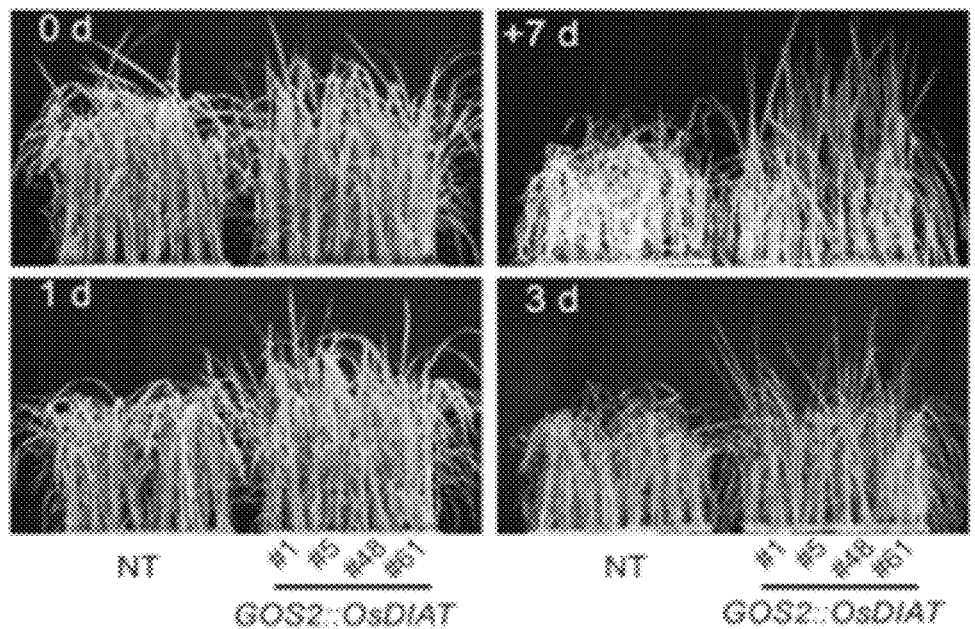
Figure 2D:
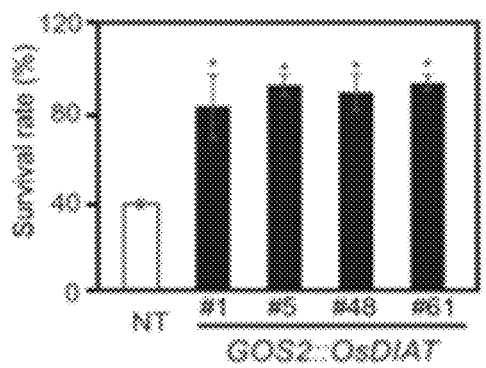
Figure 2E:
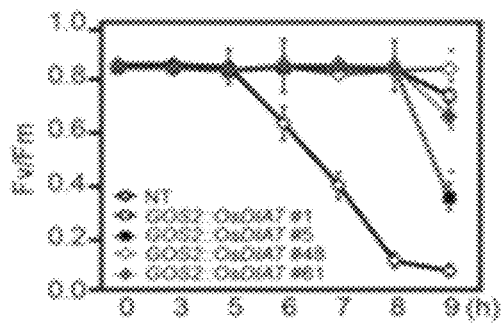
Figure 2F:
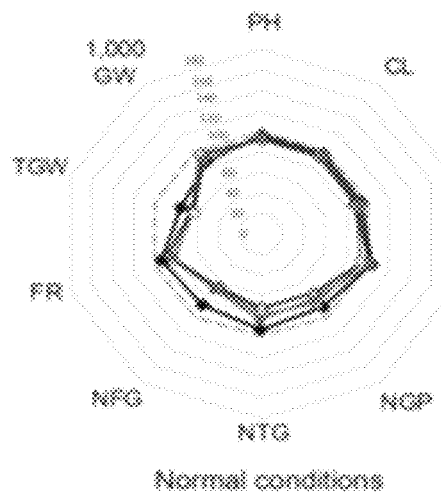
Figure 2G:
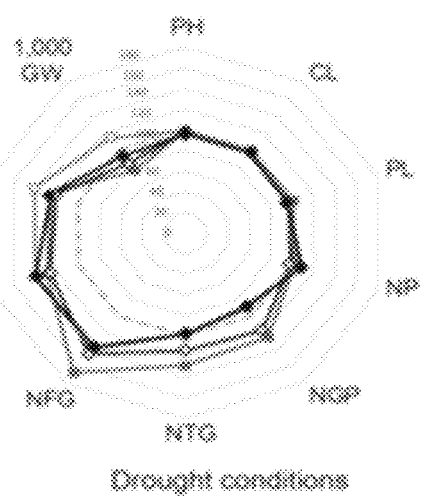

To determine the potential function of DIAT gene relating to drought tolerance, four independent lines of DIAT-overexpressing transgenic plant (GOS2::DIAT) (i.e., #1, #5, #48, and #61) were chosen based on the expression levels of DIAT in transgenic plants (FIG. 2a). To compare the performance of plants under drought conditions, the selected DIAT-overexpressing transgenic plants and non-transgenic plants (NT, Dongjin) were exposed to drought stress. Soil moisture contents measured to monitor degree of drought treatments showed similar rate of decrease indicating that stress treatments were uniformly applied across the plants (FIG. 2b). Drought induced symptoms, such as leaf rolling, wilting, and loss of chlorophyll appeared earlier in NT plants compared to those in DIAT-overexpressing transgenic plants during drought stress treatments (FIG. 2c). The DIAT-overexpressing transgenic plants also showed better recovery rates compared to NT plants after being relieved from drought stress (FIG. 2c and FIG. 2d). To further verify the performance of the plants under drought conditions, the Fv/Fm values, an indicator of the photochemical efficiency of photosystem II, were measured in plants exposed to drought stress. The Fv/Fm values in NT plants started to rapidly decrease at 5 days after drought treatment, whereas OsAT-IV$^{OX}$ plants showed the decrease 9 days after the treatment (FIG. 2e). Furthermore, to determine the drought tolerance of a transgenic plant which overexpresses DIAT gene at the reproductive stage of growth, agricultural traits of the transgenic plant were examined in field drought conditions. Compared to the NT plant, the transgenic plant showed a significant increase in agronomic traits such as total grain weight (TGW), filling rate (FR), and number of filled grain (NFG). Specifically, TGW of the DIAT-overexpressing transgenic plants was 21 to 40% higher than those of the NT plants. Similarly, the grain-filling rate (26 to 39%) and number of filled grain (37 to 68%) of the DIAT-overexpressing plants were significantly higher than those of NT plants. These results support that overexpression of DIAT can enhance the tolerance of a plants against drought.

EXAMPLE 3

Figure 3:
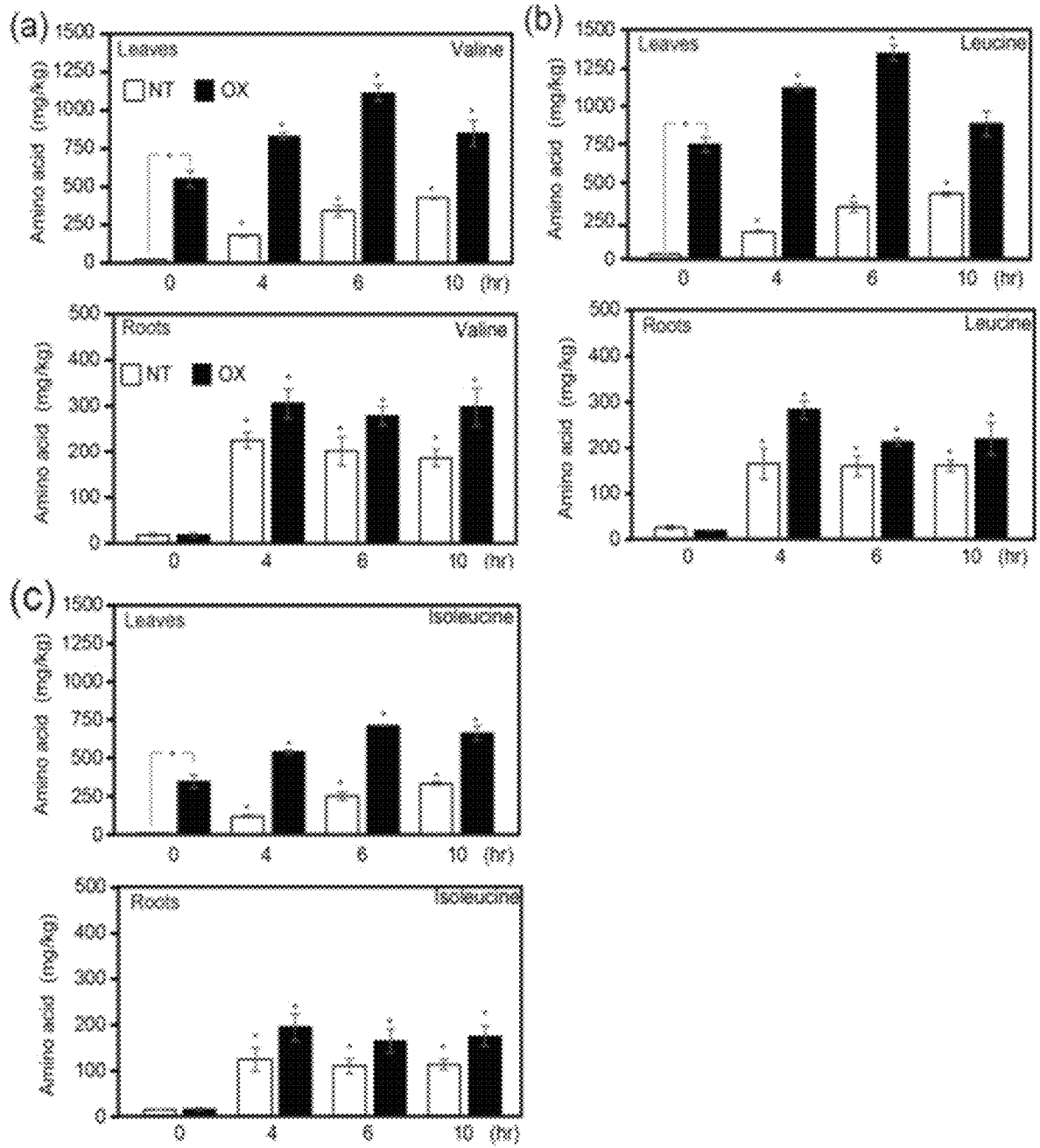
FIG. 3 shows the result of measuring content of (a) valine, (b) leucine, and (c) isoleucine, which are branched chain amino acids, in leaves and roots of non-transgenic *Oryza sativa* plants (NT) and DIAT-overexpressing transgenic rice plants (OX), which have been subjected to drought stress.

Analysis of Branched Chain Amino Acid Content in DIAT-Overexpressing Transgenic Plants As it is expected that, in Oryza sativa plant, MAT gene mediates the last amino group transfer reaction (i.e., transamination) of the process for synthesizing branched chain amino acids, content of the branched chain amino acids in a plant which overexpresses DIAT gene was analyzed. As a result, it was found that content of valine, leucine, and isoleucine, which are branched chain amino acids, has significantly increased in the leaves of the transformed plant (OX) compared to the non-transgenic plant (NT) (FIG. 3). In addition, BCAAs were further increased when plants were exposed to drought stress. In root tissues, however, the overexpression of DIAT did not significantly alter the basal BCAA levels under normal conditions although higher accumulation of BCAAs detected in OsAT-IV$^{OX}$ roots than NT roots under drought stress conditions. These results suggest that overexpression of OsAT-IV enhances the accumulation of BCAAs.

EXAMPLE 4

Figure 4:
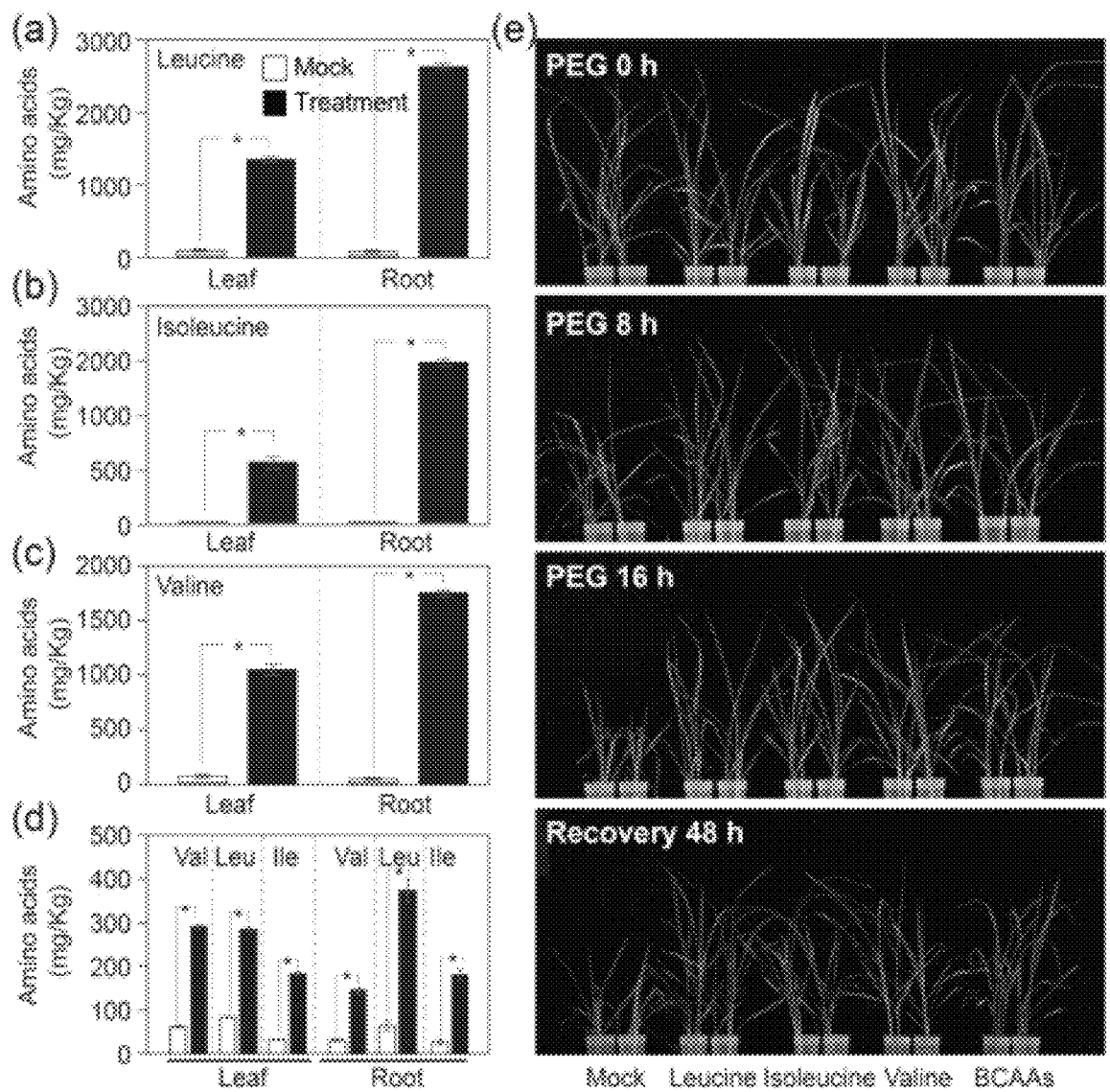
FIG. 4 shows the result of analyzing the effect of branched chain amino acids on stress tolerance of a plant, including (a) to (d) showing the result of measuring the content of valine, leucine, and isoleucine, which are branched chain amino acids contained in a rice plant, either after the distilled water treatment (Mock) or the branched chain amino acid treatment (Treatment), and (e) showing the result of determining the tolerance of a rice plant pre-treated with distilled water (Mock), leucine, isoleucine, valine and combination of the three branched chain amino acids (BCAAs) under osmotic stress conditions driven by PEG treatment.

Analysis of Plant Tolerance for Stress According to Treatment with Branched Chain Amino Acids To determine whether or not the tolerance for drought stress of a plant which overexpresses DIAT gene is induced by increased content of branched chain amino acids, the responses of rice plants pre-treated with exogenous BCAAs was examined under osmotic stress conditions driven by PEG treatment. To increase internal BCAA levels, rice roots were pre-treated with valine ((a) of FIG. 4), leucine ((b) of FIG. 4), isoleucine ((c) of FIG. 4) or combination of the three BCAAs ((d) of FIG. 4). As a result of measuring the content of branched chain amino acids in non-transgenic plant, it was found that exogenous application of branched chain amino acids applied are effectively absorbed into the plant roots and leaves ((a) to (d) of FIG. 4). BCAA pre-treated plants were then transferred to a PEG solution and monitored osmotic stress-induced symptoms in the plants. During PEG treatments, osmotic stress-related symptoms such as leaf rolling and wilting appeared earlier in mock-treated plants than BCAA pre-treated either individually or a combination of three BCAAs ((e) of FIG. 4). Pre-treatments of BCAA also increased recovery of plants after being relieved from osmotic stress by transferring to a normal growth media ((e) of FIG. 4). These results suggest that increased content of branched chain amino acids in plant can induce tolerance of a plant for osmotic stress.

What is claimed is:

1. A method for enhancing drought stress tolerance of a plant compared to a wild type plant, the method comprising:
   transforming a cell of the plant with a recombinant vector which includes a gene encoding a drought-induced aminotransferase(DIAT) protein consisting of the amino acid sequence of SEQ ID NO: 2 to overexpress the gene encoding the DIAT protein; and
   regenerating a plant from the transformed plant cell.

2. A method for producing a transformed plant with enhanced drought stress tolerance compared to a wild type plant, the method comprising:
   transforming a plant cell with a recombinant vector containing a gene encoding a drought-induced aminotransferase protein consisting of the amino acid sequence of SEQ ID NO: 2; and
   regenerating a plant from the transformed plant cells.

3. A transformed plant with enhanced drought stress tolerance produced by the method of claim 2.

4. A transformed seed of the transformed plant of claim 3.

* * * * *

SEQUENCE LISTING

<160> NUMBER OF SEQ ID NOS: 8

<210> SEQ ID NO 1
<211> LENGTH: 1023
<212> TYPE: DNA
<213> ORGANISM: Oryza sativa

<400> SEQUENCE: 1

```
atgcaagggg aacaccatga ccatgtccct gtctacgagt caggcaccga ggtgttccaa      60
aagcttcagg agaaatggaa ttccaccaag cacaagcgat accgcgcgat gtactccagc     120
gtcgtcggcg gaatcatcct cgatccatcg atgatggtca tccccatcga cgatcacatg     180
gtccacagag gccatggcgt cttcgacacc gccatgcttt ccgacgggta cctgtatgag     240
ctggattcgc acttggatcg gctgctgcta tctgcatcca aagcaaagat cagctcccca     300
ttctcccgcg aaacacttcg cgccattttg gtgcagatga cggctgcgtc caagtgcagg     360
aatggctcga tcaagtactg gctcagcgcc ggccccggcg acttcctcct ctcgccaaag     420
ggctgcactg cgccggcgtt ctacgccgtc gtcatcgcgt ccgccgccgc cgccgccgcc     480
ggcgggcacc cgcggctcag ggagggcgtg agggcgatca cgtcgacggt gccgatgaag     540
gacccgttct cgcggcgat gaagagcgtc aactacctgg cgaacgcgct ggccatggcg     600
gaggcagagg agcgcggcgc gtacgcgtcg gtgtgggtgg acggcgacgg gggcgtggcg     660
gagggcccga tgatgaacgt ggcgttcgtc acgggcggcg gcgacctggt ggtgccggcg     720
ttcgacaggg tcctcagcgg gtgcacggcg aggcggctgc tcgcgctggc gcccaggctg     780
gtggacgccg gcgtgctcag gagcgtcggc gcggcgagga tctccgccgc cgacgcgagg     840
aggtgcgccg agatgatgtt cgtcggcagc ggcctcccgt tgctgcccat cgtcgaatgg     900
gacggccagc cggttggcga tggtcaagtg gggaaaattg cccttgccct atctgacatg     960
ctttgcgaag acatcaaggc cggtctcgac agagtacttg ttccttatga tcaagcgagc    1020
tag                                                                   1023
```

<210> SEQ ID NO 2
<211> LENGTH: 340
<212> TYPE: PRT
<213> ORGANISM: Oryza sativa

<400> SEQUENCE: 2

```
Met Gln Gly Glu His His Asp His Val Pro Val Tyr Glu Ser Gly Thr
1               5                   10                  15

Glu Val Phe Gln Lys Leu Gln Glu Lys Trp Asn Ser Thr Lys His Lys
            20                  25                  30

Arg Tyr Arg Ala Met Tyr Ser Ser Val Val Gly Gly Ile Ile Leu Asp
        35                  40                  45

Pro Ser Met Met Val Ile Pro Ile Asp Asp His Met Val His Arg Gly
    50                  55                  60

His Gly Val Phe Asp Thr Ala Met Leu Ser Asp Gly Tyr Leu Tyr Glu
65                  70                  75                  80

Leu Asp Ser His Leu Asp Arg Leu Leu Leu Ser Ala Ser Lys Ala Lys
                85                  90                  95

Ile Ser Ser Pro Phe Ser Arg Glu Thr Leu Arg Ala Ile Leu Val Gln
            100                 105                 110

Met Thr Ala Ala Ser Lys Cys Arg Asn Gly Ser Ile Lys Tyr Trp Leu
        115                 120                 125

Ser Ala Gly Pro Gly Asp Phe Leu Leu Ser Pro Lys Gly Cys Thr Ala
```

| | | 130 | | | 135 | | | 140 | | | |
|---|---|---|---|---|---|---|---|---|---|---|---|

Pro Ala Phe Tyr Ala Val Val Ile Ala Ser Ala Ala Ala Ala Ala
145                 150                 155                 160

Gly Gly His Pro Arg Leu Arg Glu Gly Val Arg Ala Ile Thr Ser Thr
            165                 170                 175

Val Pro Met Lys Asp Pro Phe Phe Ala Ala Met Lys Ser Val Asn Tyr
            180                 185                 190

Leu Ala Asn Ala Leu Ala Met Ala Glu Ala Glu Arg Gly Ala Tyr
        195                 200                 205

Ala Ser Val Trp Val Asp Gly Asp Gly Val Ala Glu Gly Pro Met
    210                 215                 220

Met Asn Val Ala Phe Val Thr Gly Gly Gly Asp Leu Val Val Pro Ala
225                 230                 235                 240

Phe Asp Arg Val Leu Ser Gly Cys Thr Ala Arg Leu Leu Ala Leu
                245                 250                 255

Ala Pro Arg Leu Val Asp Ala Gly Val Leu Arg Ser Val Gly Ala Ala
            260                 265                 270

Arg Ile Ser Ala Ala Asp Ala Arg Arg Cys Ala Glu Met Met Phe Val
        275                 280                 285

Gly Ser Gly Leu Pro Leu Leu Pro Ile Val Glu Trp Asp Gly Gln Pro
    290                 295                 300

Val Gly Asp Gly Gln Val Gly Lys Ile Ala Leu Ala Leu Ser Asp Met
305                 310                 315                 320

Leu Cys Glu Asp Ile Lys Ala Gly Leu Asp Arg Val Leu Val Pro Tyr
                325                 330                 335

Asp Gln Ala Ser
        340

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
caccatgcaa ggggaacacc atgacca                                        27

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ctagctcgct tgatcataag ga                                             22

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tcgagccatt cctgcacttg                                                20

<210> SEQ ID NO 6

```
<211> LENGTH: 20
<212> TYPE: DNA
<213> ORGANISM: Artificial Sequence
<220> FEATURE:
<223> OTHER INFORMATION: primer

<400> SEQUENCE: 6
tcgagccatt cctgcacttg                                              20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
atggagctgc tgctgttcta                                              20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ttcttccatg ctgctctacc                                              20
```